(12) United States Patent
Berndt

(10) Patent No.: US 6,528,018 B1
(45) Date of Patent: Mar. 4, 2003

(54) DEVICE FOR HANDLING LIQUIDS FOR ANALYTICAL PURPOSES

(76) Inventor: Harald Berndt, Auf der Bokkenbredde 48, 44287 Dortmund (DE)

( * ) Notice: Subject to any disclaimer, the term of this patent is extended or adjusted under 35 U.S.C. 154(b) by 0 days.

(21) Appl. No.: 08/714,090

(22) PCT Filed: Mar. 14, 1995

(86) PCT No.: PCT/EP95/00952

§ 371 (c)(1),
(2), (4) Date: Sep. 17, 1996

(87) PCT Pub. No.: WO95/25280

PCT Pub. Date: Sep. 21, 1995

(30) Foreign Application Priority Data

Mar. 17, 1994 (DE) .......................................... 44 09 073

(51) Int. Cl.$^7$ ........................ G01N 30/02; G01N 30/22; G01N 30/36
(52) U.S. Cl. .......................... 422/70; 422/81; 422/100; 422/103; 436/50; 436/52; 436/147; 436/180; 436/171
(58) Field of Search ................................ 250/281, 288; 356/312; 436/52; 422/81, 100, 103; 456/52, 147, 180; 73/64.45

(56) References Cited

U.S. PATENT DOCUMENTS

| | | | | |
|---|---|---|---|---|
| 4,730,111 A | * | 3/1988 | Vestal et al. ................. | 250/288 |
| 4,886,359 A | * | 12/1989 | Berndt ........................ | 356/312 |
| 4,902,891 A | * | 2/1990 | Vestal ........................ | 250/281 |
| 4,981,356 A | * | 1/1991 | de Loos-Vollebregt ..... | 356/312 |
| 5,066,382 A | * | 11/1991 | Weinberger et al. | |

* cited by examiner

Primary Examiner—Michael Pak
(74) Attorney, Agent, or Firm—Mallinckrodt & Mallinckrodt

(57) ABSTRACT

An apparatus and method for handling flowing liquids for analytical purposes such as for introduction of liquid samples in atomic spectroscopy and carrying out a continuous flow digestion process at high temperture and pressure. The appaartus comprises a high-pressure pump for conveying a liquid from a reservoir into a tube having an elongate cavity connected to the high-pressure pump outlet. A heating device is arranged so as to heat the liquid in the cavity to a predetermined temperature and a restrictor is arranged downstream of the cavity at the opposite end of the tube. The restrictor is dimensioned relative to the conveying capacity of the high-pressure pump so that liquid in the cavity is maintained at a pressure which is higher than the saturated vapor pressure of the liquid at the predetermined temperture such that no vapor forms within the cavity. When used for introducing samples in spectroscopy, the liquid is a sample which, forming an aerosol, emerges from the restrictor in the form of an aerosol. The arrangement can also be used for solubilizing liquid samples, the liquid being formed by a sample liquid mixed with a solubilizer.

41 Claims, 12 Drawing Sheets

DEVICE FOR HANDLING LIQUIDS FOR ANALYTICAL PURPOSES

This application claims priority under 35 U.S.C. 119 of German application number P 44 09 073.0 filed Mar. 17, 1994.

TECHNICAL FIELD

The invention relates to a device for the handling of flowing liquids for analytical purposes.

One aspect is carrying out a chemical reaction at high temperature. The handling may, however, also consist in nebulization of the liquid to form an aerosol.

In particular, the invention relates to a device for the sample introduction in atomic spectroscopy, wherein a sample liquid under pressure is directed through a heated tube by means of a high pressure pump for forming an aerosol.

Another application of the invention is a device for carrying out a digestion process with a liquid at high temperature and under high pressure in a continuous flow.

The invention may also be used to carry out both a digestion process with a liquid and, subsequently, to form an aerosol for the sample introduction for atomic spectroscopy purposes, using the same apparatus.

BACKGROUND ART

A prior art method of nebulizing liquids consists in pressing the liquid by means of a high pressure pump through a heated tube. Such a device is called "thermospray". In such a device, the liquid is vaporized completely or partly. On the way of the liquid through the tube, at first, bubbles are progressively formed within the liquid. Then the flowing medium is predominantly vapor with less and less liquid droplets. In the end section of the tube, a vapor jet of high flow speed is formed. The tube is a narrow capillary.

In a prior art thermospray assembly ("Spectrochimica Acta" Vol. 43 (1988), 983–987) a quartz capillary encased by a steel tube is used. Pure vapor phase emerges from the exit of the quartz capillary. A similar assembly with a quartz capillary in a heated stainless steel tube for the sample introduction into an IPC is described in "Journal of Analytical Atomic Spectrometry", Vol. 4 (1989), 213–217. Another assembly ("Spectrochimica Acta" Vol 41 (1986), 1287–1298) uses a directly heated metal capillary.

Published U.K. Patent Application No. 2,240,176 shows an apparatus for nebulizing liquids, for example from a liquid chromatograph, as aerosol into a mass spectrometer or some other gas detector. There, an aerosol is generated by pressing a liquid to be nebulized through an inner tube and pressing a well heat conducting gas such as hydrogen or helium through an outer tube concentric thereto. The gas is heated by a heater. Thereby, the liquid in the inner tube is vaporized, thermally nebulized droplets being formed similar to a conventional thermospray. This is a kind of combination of thermospray and pneumatic nebulization, which, according to the description, represents essentially a heated, pneumatic nebulization.

Furthermore, it is known to direct an aerosol emerging from a thermospray assembly by means of a carrier gas through a cooler, in order to condense the solvent. The condensed solvent is sucked off to a waste vessel at the bottom of a U-shaped cooler (company brochure "SEPARATOR" of VESTEC Corporation, 9299 Kirby Drive, Houston, Tex. 77054).

Furthermore, it is known to de-solvatize aerosols, which are generated by a pneumatic nebulizer for the sample introduction for atomic spectroscopy, by vaporization, and to subsequently condense the vapor by a cooler. In this way, the liquid solvent is removed and a dry aerosol is obtained ("Spectrochimica Acta" Vol 23B (1968), 553–555). The same type of drying the aerosol is used in commercially available ultrasonic nebulizers for the IPC-spectrometry.

From German Patent No. 3,521,529 (=European Patent No. 0,208,901 B=U.S. Pat. No. 4,886,359) a device for nebulizing sample liquid for spectroscopic purposes is known, wherein a liquid to be nebulized is pumped at high pressure by a pump through a nozzle and is nebulized by the nozzle. In this apparatus, the pump is a high pressure pump designed as a separate assembly for generating a minimum pressure of 3 MPa (30 bar). Preferably, this is a continuously delivering multi-piston pump as used for high pressure liquid chromatography (HPCL). The nozzle connected to the pump through a conduit has a smallest cross sectional area for the flow of less than $1.3 \cdot 10^{-9}$ $m^2$.

Published German Patent Application No. 3,026,155 shows a method of pneumatically nebulizing liquids by means of a pressurized gas stream concentric to a liquid carrying tube, wherein the nebulized liquid is subsequently vaporized by microwave radiation. According to Published German Patent Application No. 3,233,130, a liquid sample is vaporized from a carrier by supplying electrical energy. Solid samples are incinerated by applying infrared radiation. In this way a dry aerosol is generated and is supplied to a spectrometer.

Furthermore, digestion processes under high pressure and at high temperature for analytical purposes are known. In such processes, the liquids to be digested are filled into thick-walled containers of stainless steel which contain an inert inner container of PTFE (digestion bomb). These containers are closed by threaded caps. Then the containers are heated by a heater. This is a batch process. This process is time consuming since the containers cannot be opened before they have been cooled down.

DISCLOSURE OF THE INVENTION

It is the object of the invention, to provide an advantageous device for handling flowing liquids, which permits the liquid to be kept at high temperature.

More specifically, it is an object of the invention to improve the sample introduction in spectroscopy.

A further, still more specific object of the invention is to facilitate and speed up the digestion process of liquids for analytical purposes.

According to the invention, this object is achieved by a device for handling flowing liquids, comprising a high pressure pump for feeding the liquid, a cavity connected with the outlet of the high pressure pump, means for heating the cavity and a restrictor connected in series with the cavity at the outlet side thereof, the restrictor being dimensioned relative to the delivery of the high pressure pump such that it ensures a substantially elevated pressure in the cavity as compared to atmospheric pressure.

Such a device permits heating of a liquid in the cavity in through-flow to high temperatures without development of vapor. Development of vapor is prevented by the high pressure generated by the high pressure pump. In the assembly of the invention, a quasi-closed system is provided, in which the liquid is under a pressure which lies above the saturated vapor pressure of the liquid. Under this pressure, the liquid can be heated to high temperatures. Preferably the cavity has such a low flow resistance as compared with the flow resistance of the restrictor, that a substantially constant pressure prevails in the cavity over the length thereof.

If the liquid emerges through a restrictor designed as a nozzle and is expanded thereby, part of the super-heated liquid is vaporized. Then two influences cooperate in finely nebulizing the liquid: On one hand, the liquid is nebulized, when leaving the nozzle, by "high pressure" nebulization of the type described in German Patent No. 3,521,529. On the other hand, however, there is also spontaneous nebulization by vaporization of part of the liquid. Thereby, a very finely nebulized aerosol can be generated. The yield of the sample for introduction into a spectrometer is improved.

With another use of the assembly of the invention, the high temperature which can be achieved under high pressure is used to initiate chemical reactions, for example to carry out a digesting process. This is done continuously in through-flow. As no vapor develops, no crystallized depositions occur even when using highly concentrated salt solutions.

Modifications of the invention are subject matter of the dependent claims.

Embodiments of the invention are described in greater detail hereinbelow with reference to the accompanying drawings.

DESCRIPTION OF PREFERRED EMBODIMENTS

Figure 1:
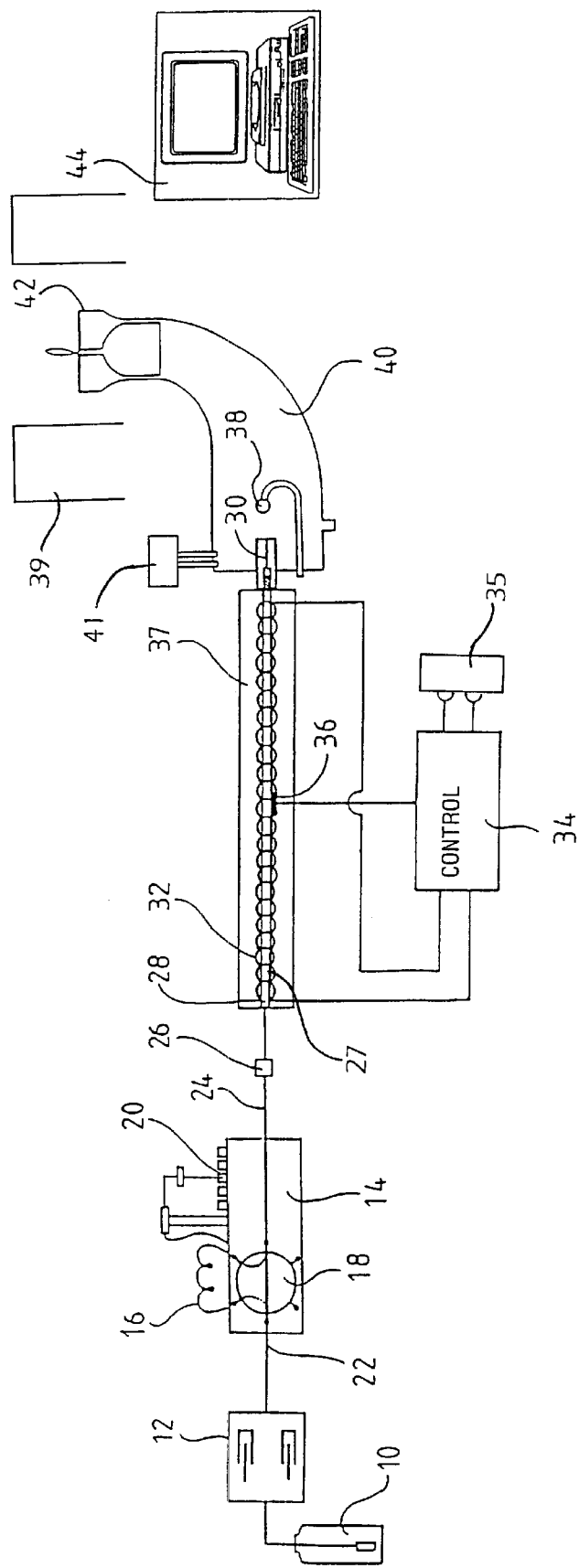
FIG. 1 shows a first embodiment of the assembly of the invention for introducing a finely nebulized aerosol into the mixing chamber of a burner for flame atomic absorption spectroscopy.

Referring to FIG. 1, numeral 10 designates a source of liquid, namely a supply vessel containing a carrier liquid. The carrier liquid is drawn off from the vessel 10 by a multi-piston high pressure pump 12. Such pumps are commercially available for high pressure liquid chromatography (HPCL). The multi-piston high pressure pump feeds the carrier liquid under high pressure to a autosampler 14. Also such autosamplers are commercially available for the high pressure liquid chromatography. In its simplest form, the autosampler has a sample loop 16, an automatic valve 18 and a dosing device 20. In a first operating position, an inlet 22 connected to the multi-piston high pressure pump 12 communicates directly with an outlet 24. The sample loop 16 is connected to the dosing device 20 and is filled with a sample liquid. In a second operating position of the automatic valve 18, the sample loop 16 is connected into the carrier liquid flow flowing from the multi-piston high pressure pump 12 to the outlet 24. Thereby the sample liquid dosed into the sample loop is pressurized to the pressure of the carrier liquid and is displaced out of the sample loop 16 by the carrier liquid and is carried along by the carrier liquid. The autosampler can be controlled by an internal programmer. The autosampler 14 may, however, also be controlled by an external control.

In a simpler embodiment, the autosampler 14 may be replaced by a commercially available manually, electrically or fluid actuated sample injection valve. Such valves may also be actuated automatically through a computer 44 with an interface with HPLC-software.

From the outlet 24, the carrier liquid flows through a filter 26. This filter may be a titanium sieve filter with 3 $\mu$m mesh also known from high pressure liquid chromatography. Downstream of the filter, the carrier liquid flows through a cavity 28 which, at the outlet side thereof, is closed by a restrictor or flow restrictor 30 with a nozzle. The cavity is formed by a hollow body in the shape of tube 27 made of a metal alloy having high chemical resistance. A tube of a 80:20- or 75:25-platinum iridium alloy has been found particularly advantageous. The tube is surrounded by a heater coil 32. The heater coil 32 is energized by a control 34. The control 34 receives an actual temperature value from a temperature sensor 36 and maintains a desired temperature in the tube. The heater coil is surrounded by heat insulation 37.

Liquid pressed through the tube under high pressure is nebulized by the restrictor 30. A spherical converter body 38 is arranged in front of the restrictor 30. The aerosol cloud formed in this way enters the gas mixing chamber 40 of a burner 42 for the flame atomic absorption spectroscopy.

The atomic absorption measurements and the autosampler 14 can be controlled by a computer 44. With the aid of HPLC-software, also consecutive transient signals can be measured.

The multi-piston high pressure pump 12 provides a pressure of more than 3 MPa (30 bar) in all of the cavity 28. In a preferred embodiment, an operating pressure in the cavity of about 20 MPa is used, at any rate in general a pressure which lies above the saturated vapor pressure of the sample liquid.

The tube defining the cavity 28 is a platinum iridium tube of 15 cm length with an outer diameter of 1.6 mm and an inner diameter of 1.0 mm. The narrowest cross-section of the nozzle 30 is 20 $\mu$m and thus is essentially smaller than the cross-section of the tubular cavity 28.

The heater coil 32 consists of a heater wire insulated by fiber glass. The heat insulation is a commercially available, heat-resistant insulating hose. The control 34 is a PID-controller having a 24 volts, 10 amperes AC low voltage power supply. The temperature sensor is a Pt 100-thermocouple. The operating temperature is usually 300° C.

Instead of by means of the heater coil 32, the cavity 28 defined by a metal tube can also be heated directly by electrical current; this is true also for the tubes described herinbelow which contain a metal sheath. When using a Pt/Ir-capillary of 300 mm length, an outer diameter of 1.5 mm, an inner diameter of 1 mm, a flow rate of 3 ml/min, a temperature of 300° C. was measured with a power consumption of about 70 watts (about 3.5 volts, about 20 amperes). A similar capillary of 0.9 mm outer diameter and 0.6 mm inner diameter resulted in the same temperature with the same flow rate and with a power consumption of about 58 watts (about 5.5 volts, about 10.5 amperes).

The cavity 28 may also be defined by a tube consisting of a composite material. Another possibility is that the cavity is defined by a high pressure capillary of stainless steel which is coated, on its inner surface, with PTFE. The cavity may be defined by a PTFE-hose encased by steel fabric. It is also possible to define the cavity by a metal tube into which a plastics hose has been drawn in or which is lined with glass on its inner surface (GLT, glass lined tubing, a commercially available HPLC-capillary). The cavity can also be defined by a quartz tube.

The cavity 28 can also be defined by a tube of tantalum. Tantalum is distinguished by its high resistance to chemicals, even at high temperatures.

A capillary of platinum-iridium can be rather short in the order of 10 to 15 cm, if temperatures of 250° C. or higher are used. In this case there will be no temperature equilibrium. Strong mixing will, however, take place at the nozzle and, thereby, temperature equalization. In this way, a very compact and low-dispersion high-efficiency nebulizer can be made.

Figure 2:
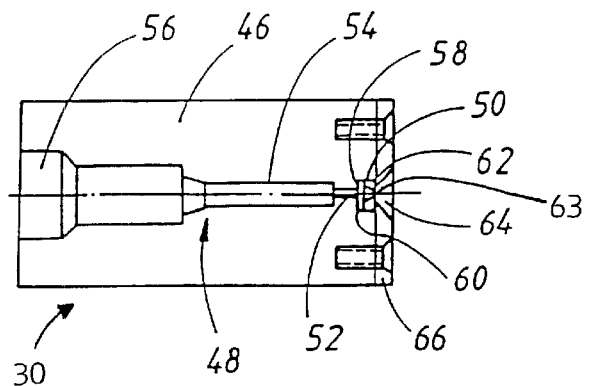
FIG. 2 shows, as a detail of the device of FIG. 1, the construction of a restrictor connected in series with the cavity on the outlet side thereof.

The restrictor 30 designed with the nozzle is shown in detail in FIG. 2. The restrictor 30 has a housing 46 with a stepped through-bore 48. The through-bore has a first section 50 on its outlet side, a reduced-diameter second section 52 adjoined therewith towards the inlet side, a further adjoining third section, and a connecting bore 56 for the tubular cavity 28 on the inlet side, a shoulder 58 being formed between the first and second sections 50 and 52, respectively. The narrowest cross sectional area of the restrictor 30 is defined by a restrictor body 62 of platinum-iridium or tantalum, which restrictor body engages the shoulder 58 through a seal 60 with a bore. The nozzle body 62 has a (not visible) through-flow aperture aligned with the second section 52, the area of the through-flow aperture being smaller than $1.3 \cdot 10^{-9}$ m$^2$. In a tested embodiment, the through-flow aperture had a diameter of 20 μm. The nozzle body 62 is retained by a plate 66, which has a conical aperture 64 and engages the edge of the nozzle body 62 with its narrow end face. The plate 66 is held on the end face of the housing 46 by screws, whereby the nozzle body 62 is held with press fit in engagement with the shoulder 58 through the seal 60. The aperture 64 is conical with a cone angle of about 90° and flares towards the outlet side.

The restrictor 30 contains the nozzle defined by the nozzle body 62 with the restrictor opening 63 in which the ratio of cross sectional diameter and length results in turbulent flow. Furthermore, the ratio of the cross sectional areas of restrictor opening and cavity is smaller than 1:5. The length of the narrowest passage or the restrictor opening 63, respectively, is equal to or smaller than the diameter of this narrowest through-flow section or restrictor opening 63, respectively.

With a circular restrictor opening 63 of 20 μm, the typical length of the narrowest through-flow section or restrictor opening 63, respectively, is about 10 μm. This is half the diameter. Typical ratios of diameter and length lie in a range of 1:1 to 1:0.4. If an inverse ratio is selected, where the length of the passage is a multiple of the diameter of the through-flow section, a passage will be formed wherein vapor may develop similar to a conventional thermospray assembly. In the case of salt containing samples, this development of vapor, in turn, will result in deposition of salts and, thereby, in clogging of the passage.

The restrictor body 62 may have different shapes, for example, it may also be cylindrical. In the illustrated embodiment, the restrictor body 62 has the form of a lamina. If the thickness of the lamina is selected to be equal to the length of the narrowest throughflow section or restrictor opening 63, respectively, (10 μm), the lamina would not have sufficient pressure resistance at prevailing pressures up to 40 MPa. For this reason, the lamina has a substantially greater thickness of, for example, 0.6 mm and contains an inner bore, which tapers in steps or continuously towards the narrowest through-flow section or restrictor opening 63, respectively, the steps being mostly rounded at their edges.

Because of the high pressure, the liquid remains in its liquid state also at the high temperatures in the cavity 28. No vapor is developed. The high pressure is enabled by the restrictor 30 at the outlet of the cavity 28, the multi-piston high pressure pump operating against this restrictor. Since no vapor is developed in the cavity, no vaporization heat is consumed. Therefore, a predetermined temperature can be reached with smaller heat supply.

Due to the fact that the volume can be made rather large and the liquid emerges through a relatively small outlet cross sectional area, a long residence time of the liquid in the cavity 28 results, as compared to prior art thermospray assemblies. This ensures that the temperature of the liquid, towards the outlet, approaches the temperature of the wall of the cavity 28, i.e. of the tube 27. The long residence time can be achieved either by a large inner diameter of the cavity 28 of, for example, 1 mm with a length of 50 mm, or by a long, thin capillary of, for example, 0.3 mm inner diameter and 5.55 m length. The tube may be coiled in order to accommodate large tube lengths in a small volume.

When the liquid emerges from the restrictor, it is nebulized by two influences: On the one hand, there is a mechanical high pressure nebulization. On the other hand, part of the liquid is vaporized by depressurization. A very fine aerosol is generated. It has been found that, with a device of the type described, an aerosol yield of 80 to 90% can be achieved. This is true also for highly concentrated salt solutions. Due to the fact that no vapor is developed within the cavity 28, there is no crystallization of salts in either the cavity or the restrictor.

The described restrictor opening 63 having a diameter of 20 $\mu$m and a flow rate of about 2.5 ml/min results in an operating pressure of 20 MPa. If a platinum-iridium capillary of 1 mm diameter is used and the diameter of the restrictor opening 63 is 20 $\mu$m, the ratio of the cross sectional areas is 1:2500.

Quantitatively, the following has been found:

With a flow rate of 2.5 ml/min and a restrictor opening of 20 $\mu$m, a flow rate of 132 m/s in the restrictor opening results. Therefore the passage time, i.e. the time during which a liquid element passes through the restrictor opening having a length of 10 μm, is 75 ns.

A turbulent flow prevails in the restrictor opening 63. Therefore a high pressure gradient from 20 MPa to 0.1 MPa occurs. The temperature drops from 300° C. in front of the restrictor opening to about 100° C. No temperature equilibrium is reached during the extremely short passage time of 75 ns. A rule of thumb of thermodynamics says that times of more than 0.5 μs are required before changes of state can ensue. Therefore, heavily super-heated liquid emerges from the restrictor opening. Partial evaporation of the liquid takes place only after the liquid has emerged from the restrictor opening 63.

Because of the converter body 38, it is also possible to nebulize liquids below their atmospheric boiling point. This permits nebulization also of very high-boiling liquids such as concentrated phosphoric acid. Also some saturated salt solutions exhibit strong rise in the boiling point relative to pure water. Even such liquids can be nebulized with the described device. Also in such case, the elevated temperature is advantageous, since the viscosity of the solution is considerably decreased with increased temperature.

Figure 10:
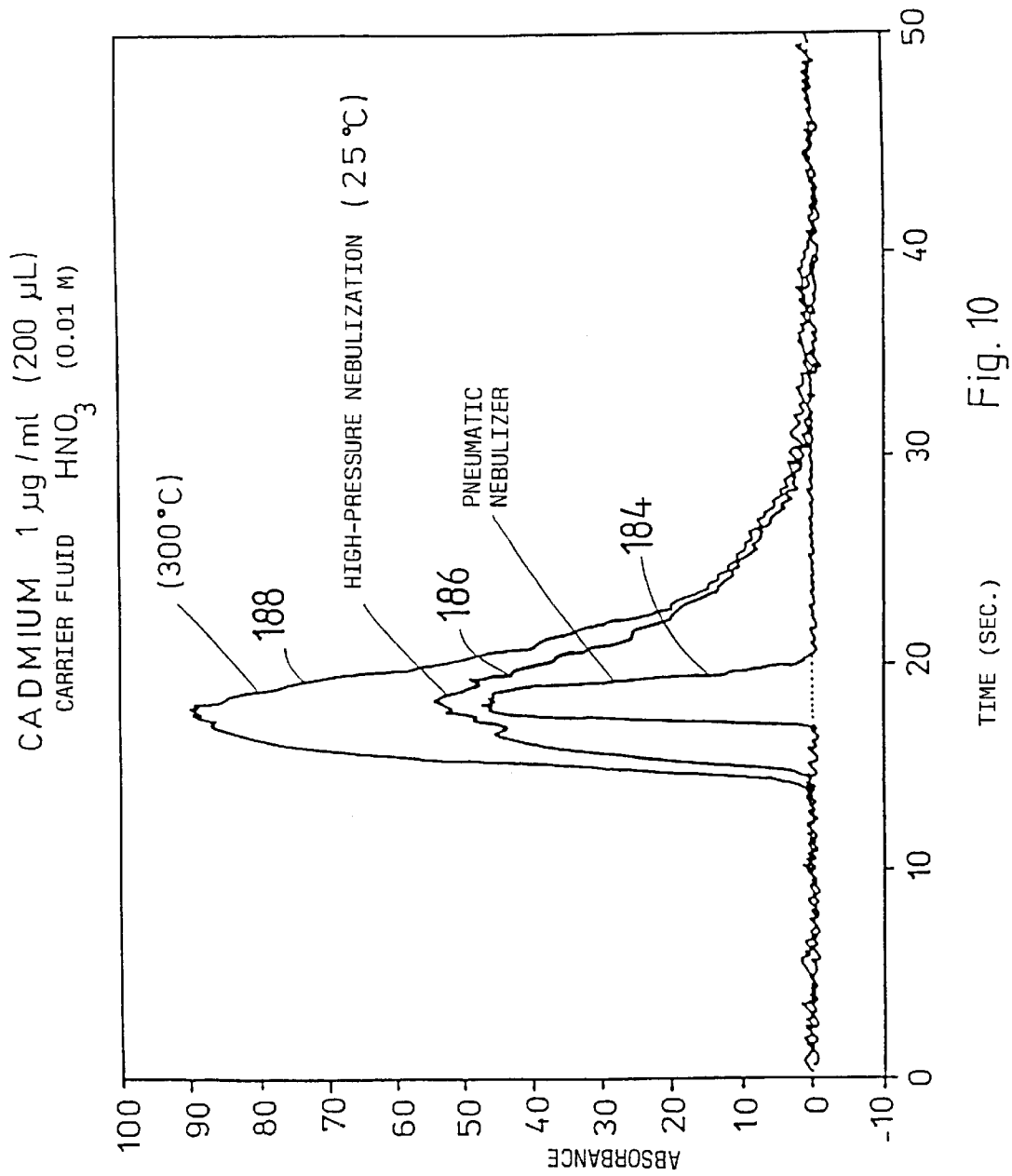
FIG. 10 shows flame-AAS signal shapes which have been taken with samples of the same type under otherwise identical conditions using different nebulizers including a nebulizer of the invention.

FIG. 10 shows analytical signal peaks obtained by flame atomic absorption spectroscopy with different types of nebulizers under otherwise identical conditions. The measurements were made with 200 μl of a solution of 1 μg/μl cadmium in a carrier liquid of 0.01-molar $HNO_3$. The time in seconds is plotted along the abscissa. The ordinate shows the measured absorbance in arbitrary units. The graph 184 shows the shape of the peak which was obtained with a pneumatic nebulizer. The graph 186 shows the peak which was achieved with high pressure nebulization in accordance with German Patent No. 3,521,529 at a temperature of 25° C. The graph 188 shows the signal shape which was obtained with a nebulization of the kind described hereinbefore at 300° C. It can be seen that the thus obtained signal is both higher and wider than the signals which are obtained with nebulization in accordance with the prior art. This is the consequence of the essentially higher yield of atomizable aerosol which can be achieved with the device described here; typically the used percentage of aerosol in a device of the present application is 80–90% of the sample liquid.

Figure 11:
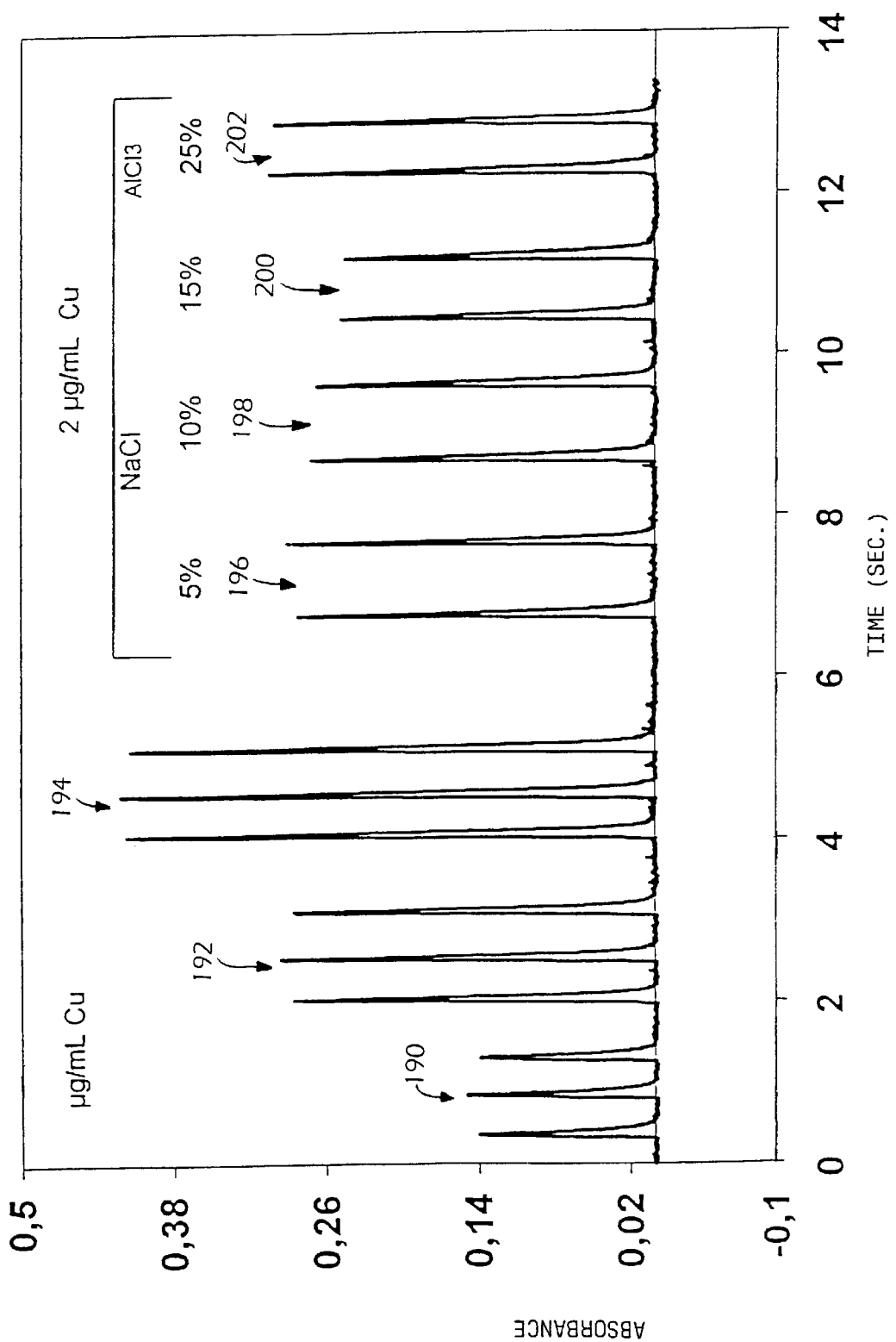
FIG. 11 shows signal shapes similar to those of FIG. 10 for different concentrations of copper solution and different concentrations of added salts.

FIG. 11 shows signal shapes which have been obtained with copper solutions making use of the apparatus described hereinbefore and of the described method. The peaks 190, 192 and 194 were obtained with solutions which contained 1, 2 and 3 μl/ml Cu, respectively. It has been found that there is good conformity of peaks of the same type and good linearity of the measurement. Different peaks 196, 198, 200 and 202 are illustrated in the right-hand part of FIG. 11, these peaks being all taken with a solution of 2 μg/ml Cu but containing increasing quantities of salts, namely 5% NaCl, 10% NaCl, 15% NaCl and 25% $AlCl_3$, respectively. It will be noticed that the measurements are virtually not affected by the added salts.

Figure 12:
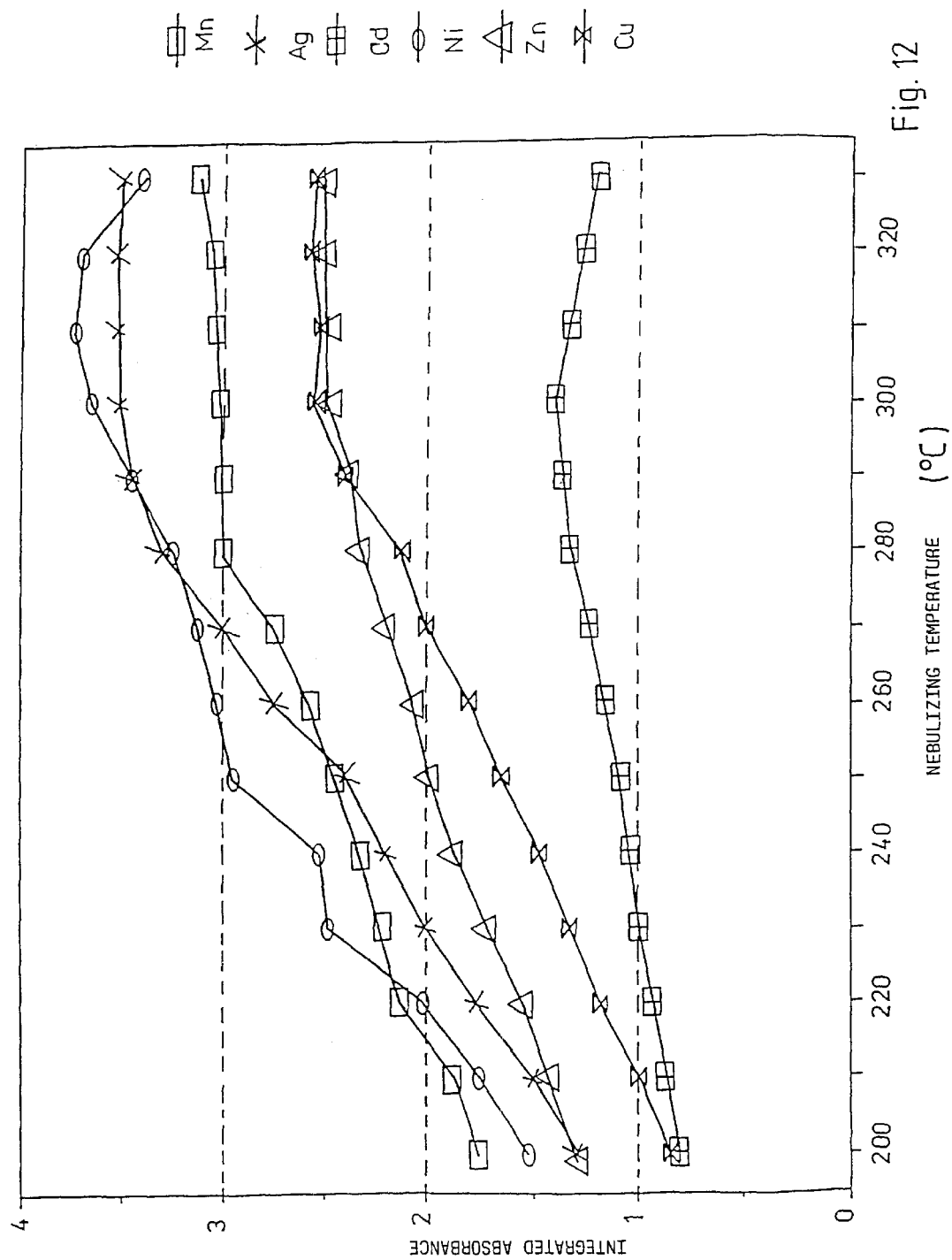
FIG. 12 illustrates, with a nebulizer of the present type, the influence of the temperature on the integrated extinction, i.e. on the integrals of peaks of the type shown in FIG. 10, with flame-AAS analysis of various metals.

FIG. 12 shows, for various metals, namely Mn, Ag, Cd, Ni, Zn and Cu, the integrated absorbance, thus the integral of the signal peaks of the kind illustrated in FIG. 10 occurring with atomic absorption spectroscopy as a function of the temperature generated within the cavity 28. It has been found, that the graphs verge on saturation or exhibit a maximum at about 300° C. Therefore, it is reasonable to operate at a temperature of 300° C., as described hereinbefore.

Figure 13:
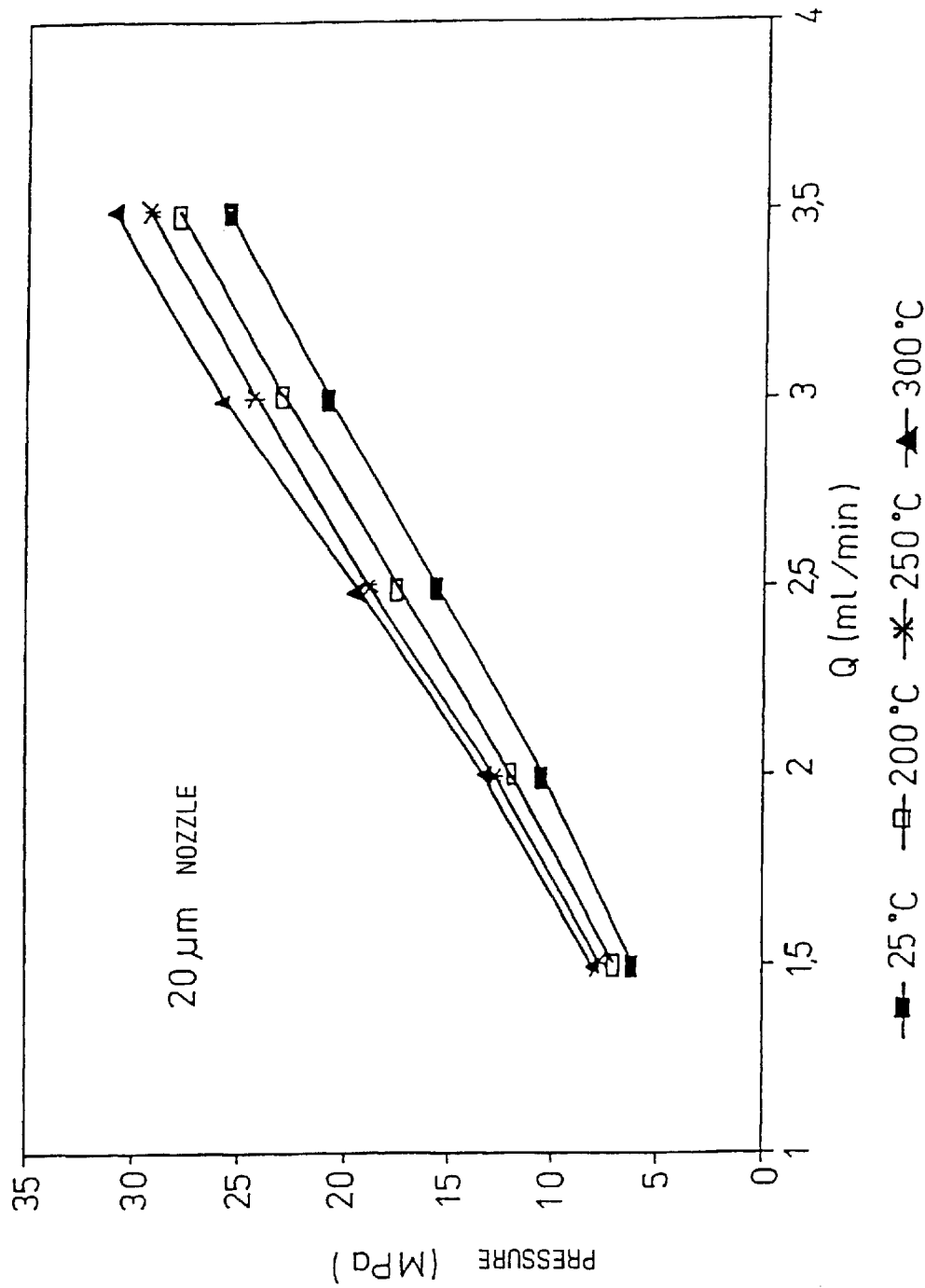
FIG. 13 shows, for an apparatus with a nozzle of 20 $\mu$m diameter, the operating pressure in the heated cavity as a function of the flow rate at different temperatures.

FIG. 13 illustrates, for the nebulizer described hereinbefore, the operating pressure prevailing in the cavity as a function of the flow rate, and this for different temperatures of the carrier and sample liquids in the cavity of 25° C., 200° C., 250° C. and 300° C.

Figure 14:
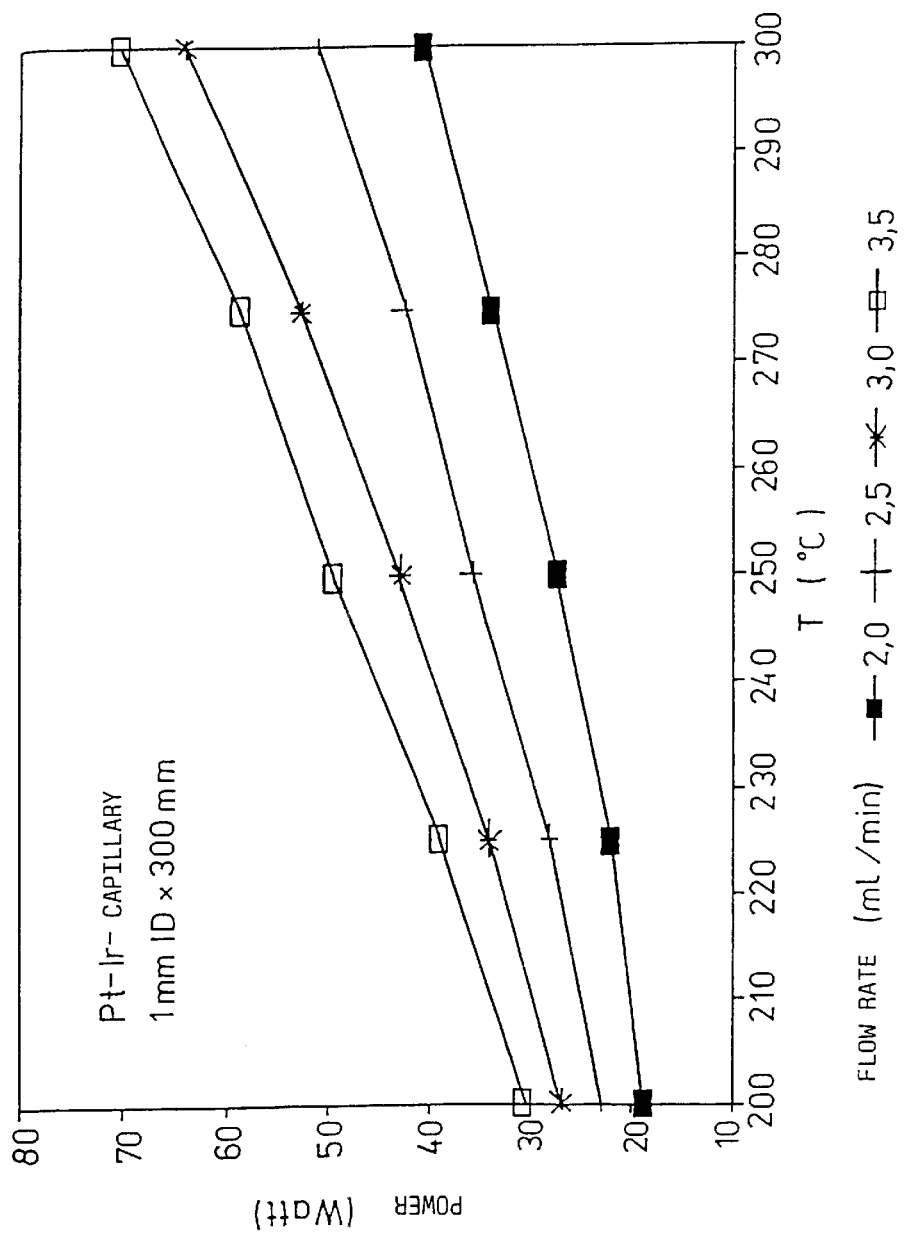
FIG. 14 shows, for a nebulizer of the present type and various flow rates, how the power consumption depends on the temperature.

FIG. 14 shows the power consumption of the heater coil 32 for a platinum-iridium capillary having an inner diameter of 1 mm and a length of 300 mm with the nebulizer described hereinbefore as a function of the temperature of the capillary, and this for different flow rates of 2.0 ml/min, 2.5 ml/min, 3 ml/min and 3.5 ml/min. It will be noticed therefrom that, contrary to the prior art thermospray assemblies with flow rates of 1 ml/min or less, also large flow rates and, thereby, large mass transport are achieved without problems with the high pressure nebulization described here, as by wide-walled capillaries a longer residence time is achieved and, in addition, less heat per unit weight of the liquid has to be supplied.

Figure 3:
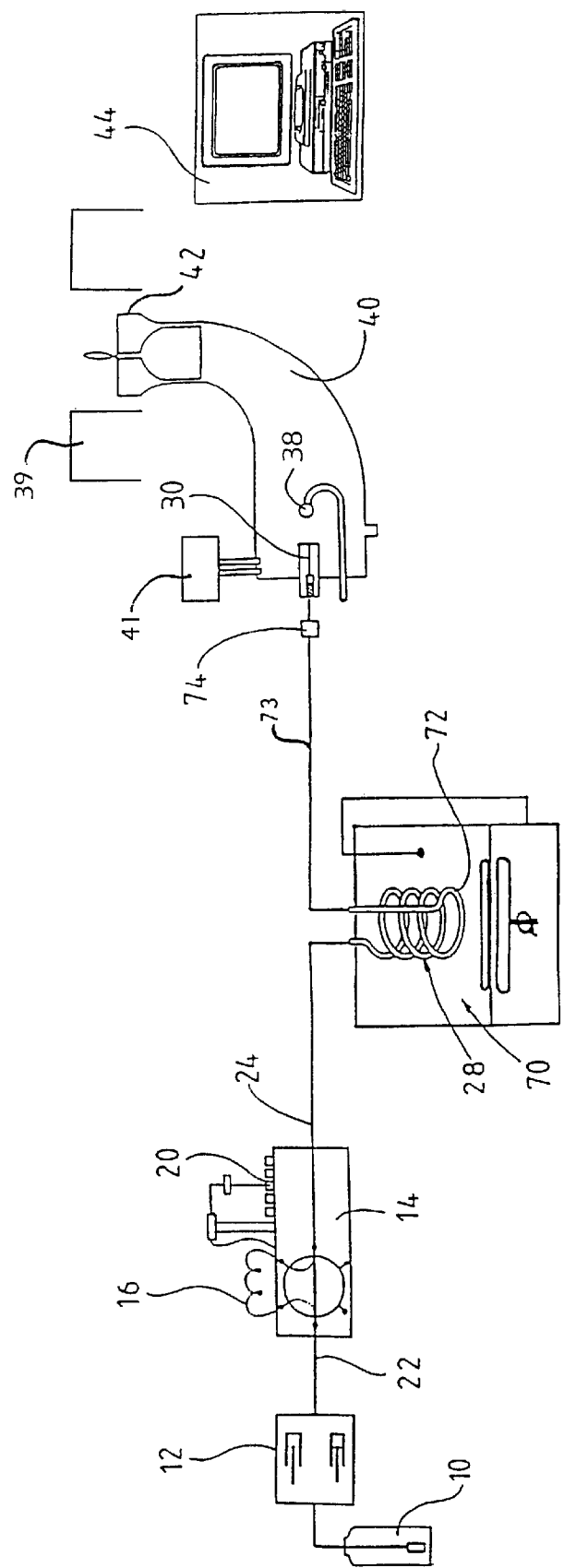
FIG. 3 shows a device similar to FIG. 1, wherein heating of the liquid in the cavity is effected by means of a temperature-controlled liquid bath.

The device of FIG. 3 is of similar construction as the device of FIGS. 1 and 2. Corresponding elements are provided with the same reference numeral in both Figures and are no longer described in detail.

In the device of FIG. 3, a temperature-controlled liquid bath 70 serves to heat the cavity 28. The cavity is formed by a coiled capillary 72 of glass-lined metal tubing, as used in high pressure liquid chromatography. The capillary 72 is connected with the restrictor 30 through a connecting conduit 73, which may be part of the capillary 72 and contains a sieve filter 74 similar to the sieve filter 26.

Figure 4:
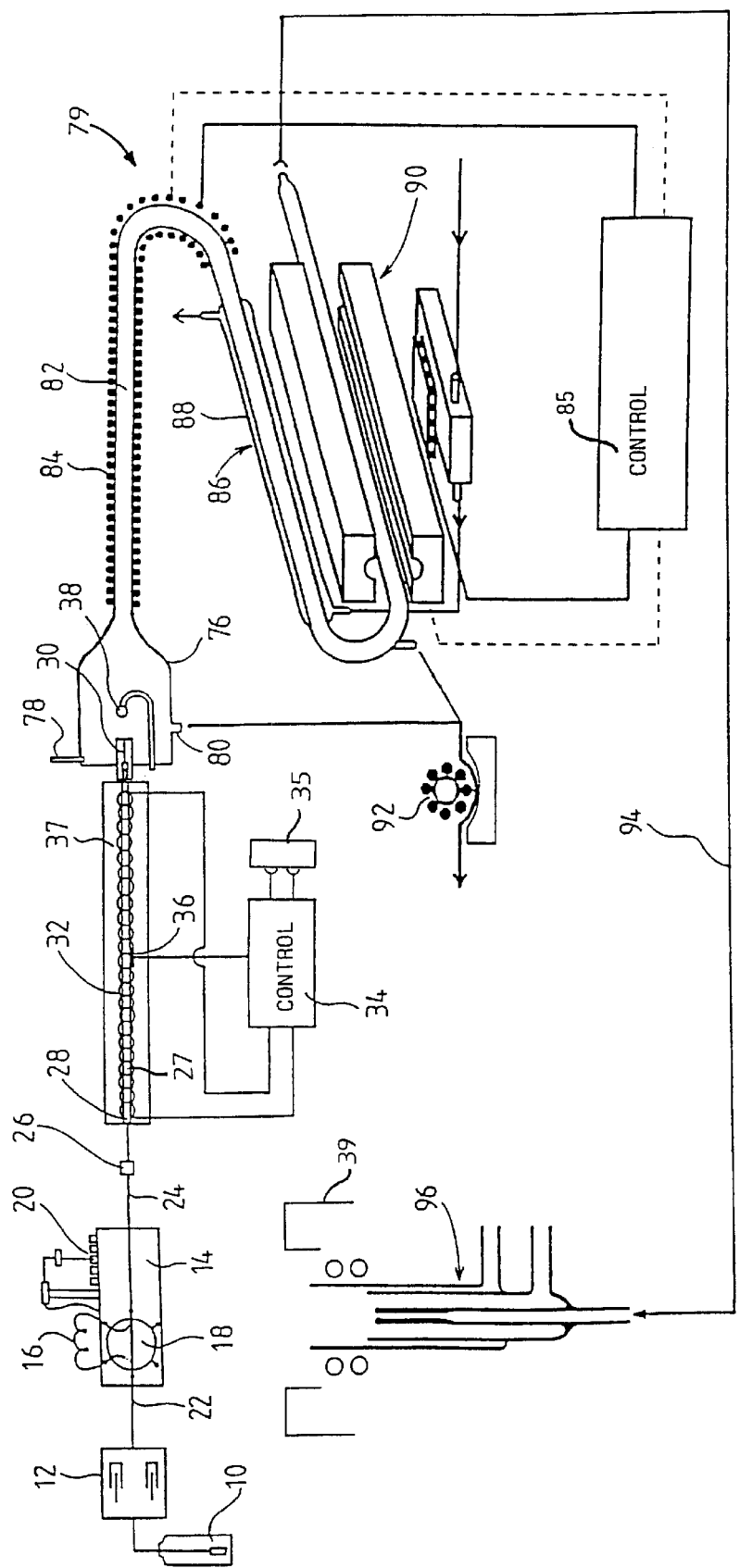
FIG. 4 shows a device for generating a "dry" aerosol for introduction into an ICP.

The device of FIG. 4 is identical with the assembly of FIG. 1 up to the restrictor 30. Corresponding elements are, also here, provided with the same reference numerals as in FIG. 1 and are no longer described in detail. The device of FIG. 4 may also be modified in the same way as described with reference to the device of FIG. 1.

The aerosol emerging from the restrictor 30 still contains droplets of solvent, in which the sample components of, for example, a solid sample are dissolved. In spite of the preceding heating up within the cavity 28, the percentage of vapor in the aerosol is low. This can be explained with reference to the example of an aqueous solution: The enthalpy of water at 179° C. amounts to 758.7 J/g (181,2 cal/g). The enthalpy of the water vapor at the same temperature amounts to 2775.9 J/g. Even if all of the water were at saturated vapor temperature prior to issuing from the restrictor opening, still 2017.2 J/g would have to be supplied, in order to completely vaporize the water after issuance from the restrictor 30. Even at a rather high temperature of 249° C., the enthalpy difference would still amount to 1720 J/g. Thus the heat supplied to the pressurized liquid is by no means sufficient to effect complete vaporization of the liquid after its depressurization.

In many cases, for example when an aerosol is introduced into an inductively coupled plasma (ICP), the proportion of solvent still contained in the aerosol interferes with the measurement. It results in undesirable dilution of the plasma. Thereby, the high frequency behavior of the plasma is affected to such extent, that strong signal noise and, eventually, extinguishing of the plasma results. In simple cases, it may be sufficient to reduce the solvent proportion in the aerosol by means of a cooled nebulizer chamber.

In general, however, it is not sufficient to cool the aerosol for "drying" the aerosol, as thereby only the vapor-state proportion of the solvent is condensed. It is necessary to supply, at first, further heat to the obtained aerosol. Only after most of the solvent still contained therein has been vaporized in this manner, the cooling will be effected.

A corresponding device of this type 79 is illustrated in FIG. 4 in combination with the device of FIG. 1. The drying means for evaporating and re-cooling the aerosol in order to remove the solvent, is known per se (for example, Article No. 1032 of Wissenschaftlicher Gerätebau Dr.-Ing. Herbert Knauer GmbH, 14163 Berlin).

The aerosol is generated, in the way described, in a spray chamber 76. A carrier gas port 78 is provided at the spray chamber 76 and argon as carrier gas is passed therethrough. A drain 80 for condensed solvent is provided on the underside of the spray chamber. A piece of tube or heating chamber 82 adjoins the spray chamber 76 and can be heated by a heater 84. The proportion of solvent still contained in the aerosol after emerging from the restrictor 30, is vaporized in the piece of tube 82. A cooling device or chamber 86 adjoins the heated piece of tube 82. The cooling device or chamber contains an upstream first stage 88 including a liquid cooler and a second downstream stage 90 including a Peltier cooler. The heater 84 and the Peltier cooler are temperature-controlled by a control 85. The cooling device 86 and the drain 80 are connected with a peristaltic pump 92 for removing the condensed solvent. The thus "dried" aerosol is directed by the carrier gas argon through a conduit 94 into an ICP-burner 96.

Figure 5:
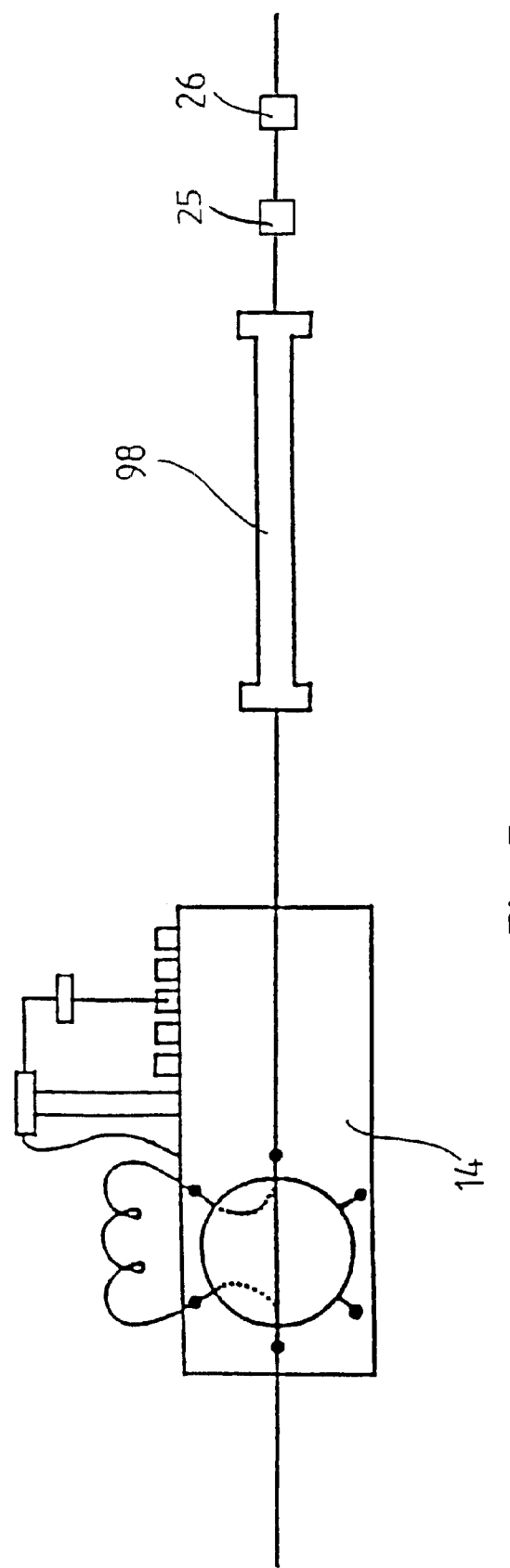
FIG. 5 shows an additional equipment comprising a HPLC-separating column interposed between a autosampler and the heated cavity.

FIG. 5 shows a modification of the device of FIG. 1. In this device, a high pressure separating column 98 for high pressure liquid chromatography is connected to the autosampler 14 downstream thereof. By inserting this high pressure separating column 98, a multitude of on-line separating and enrichment possibilities typical of HPLC for element trace analysis and for an improved element speciation technique is obtained. Contrary to a conventional coupling of HPLC-separating techniques and atomic spectroscopy, the arrangement described here is a closed high pressure flow system in the form of a high pressure nebulizer. In this respect, FIG. 5 shows a modification of the devices of FIGS. 1 to 4; the high pressure separating column 98 follows the sampling device including the autosampler 14, the automatic valve 18 and the sample loop 16 and is connected to the inlet side of the high pressure cavity 28. Fractions eluted from the high pressure separating column 98 can be introduced directly into the high pressure cavity 28, for example, when determining iron(II) and iron(III) or chrome (III) and chrome(VI) with flame AAS. Element traces in the form of complex compounds can be separated from a saturated sodium chloride solution by, for example, a C18 RP-separating column of 5 cm length. The sodium chloride matrix and the element traces reach the flame AAS-burner at different times. Thereby, interferences due to the matrix are eliminated during the flame AAS-measurement. Due to the high salt load, the burner slot will be gradually clogged. In such and other cases, it may be useful to provide a high pressure valve assembly 25 at the exit of the high pressure separating column; the valve assembly not only serves for separating the matrix in the presntly described embodiment but also is favorable for element enrichment. Then the element traces eluted from the high pressure separating column are introduced consecutively or together into the high pressure cavity and are subjected to annalysis by atomic spectrometry. This arrangement offers particular advantages also for ICP-spectrometry by solvent removal in accordance with FIG. 4, since the heated piece of tube 82 does not get into contact with the matrix whereby memory effects are avoided. Furthermore, there were tested arrangements employing pre-column techniques for preconcentrating element traces to be separated as well as further element trace concentrations and matrix separations using cation and anion exchanger columns. With the aid of a combined evaluation and control software, an autosampler and automatic valves, such on-line separations can be carried out fully automatically. It has been found useful to also carry out the atomic spectrometric signal processing of consecutive signals by means of HPLC-software.

The restrictor 30 in the devices of FIGS. 1 to 5 may, if desired, be heatable or thermally insulated.

Figure 6:
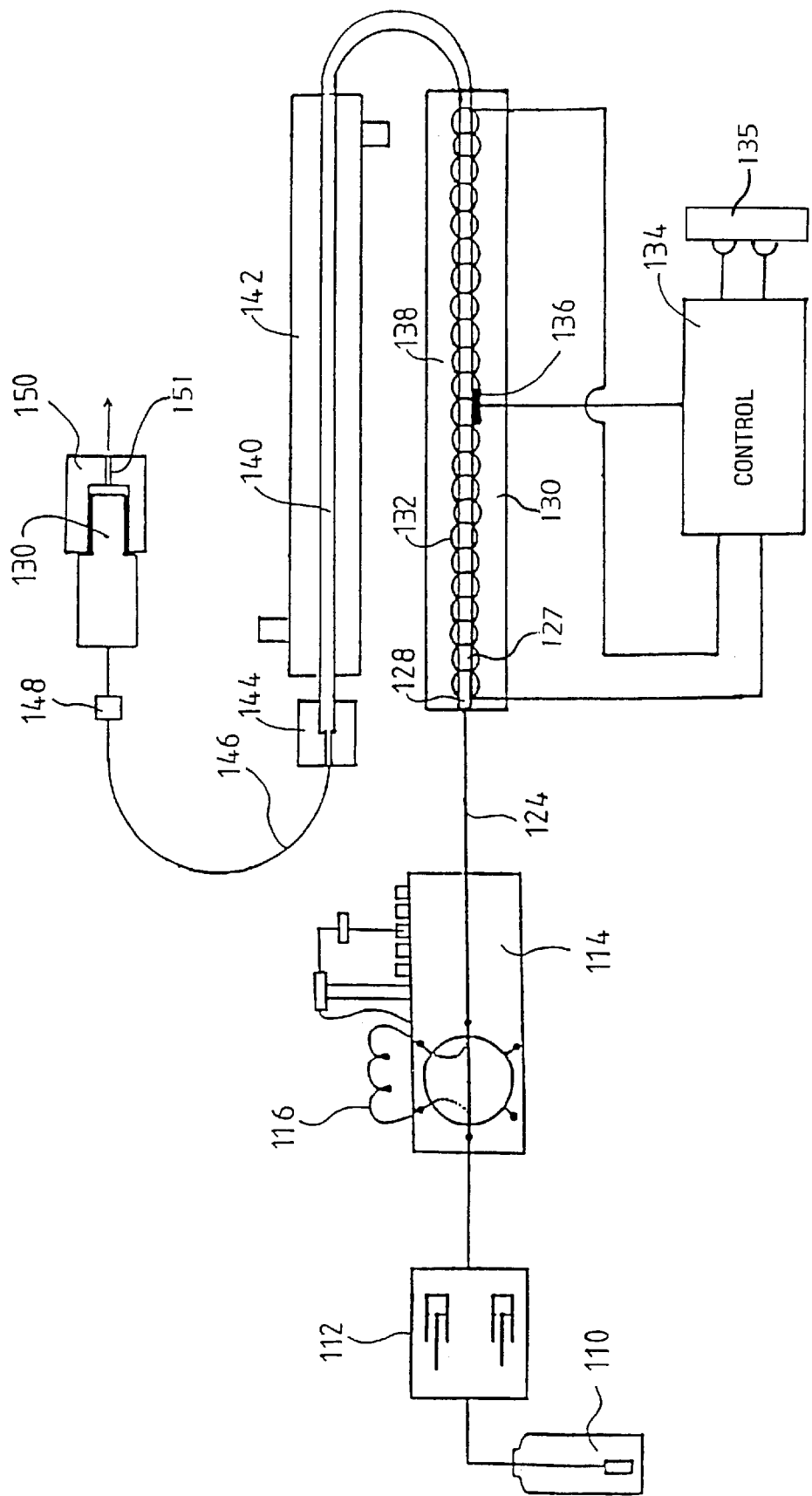
FIG. 6 shows a sample digesting system with a heated cavity, a cooling length of tubing and a following restrictor.

FIG. 6 shows a sample digesting system, in which a sample liquid together with a digestant is exposed to high temperature under high pressure for a certain time, in order to chemically digest a sample.

The sample digesting system of FIG. 6 is of similar construction as the device of FIG. 1. Referring to FIG. 6, numeral 110 designates a supply vessel or reservoir holding carrier liquid. In this embodiment, the carrier liquid contains, at the same time, a digestant or is a liquid digestant. This ensures a sufficiently high concentration of digestant also at the ends of the sample plug. Otherwise, dilution of the digestant in the sample would take place due to dispersion. The liquid digestant is taken in from the vessel 110 by a chemically inert multi-piston high pressure pump 112. The multi-piston high pressure pump 112 feeds the liquid digestant under high pressure to an autosampler 114. The autosampler 114 operates as described with reference to FIG. 1. Instead of the autosampler 114, also here, a manual or electrically or fluid operated sampling valve may be used. From the outlet 124 of the autosampler 114, the liquid digestant stream flows through a cavity 128 which is closed by a restrictor 130 at its outlet, the construction of the restrictor being to a large extent identical with that of restrictor 30. Similar to the arrangement of FIG. 1, the cavity 128 is defined by a hollow body in the shape of a tube 127 made of, a stainless steel or a metal tube coated with glass on its inside, it may, however, also consist of quartz. As before, the tube 127 can also be a high pressure capillary of stainless steel coated with PTFE on its inside, or a PTFE-hose sheathed by a steel fabric. Also here, it is possible to use a metal tube into which a plastics hose is drawn, or a quartz tube.

The tube 127 is surrounded by heating means in the form of a heater coil 132 on a part 130 of its length. The heater coil 132 is energized by a control 134. The control 134 receives an actual temperature value from a temperature sensor 136 for maintaining a desired temperature in the tube 127. The heater coil 132 is surrounded by a heat insulation 138. Instead of by the heater coil, the cavity 128, when defined by a metal tube, may also be heated directly by electric current; this is true also for the other tubes mentioned hereinbefore which contain a metal sheath. The heating power may be distributed non-uniformly over the length of the tube, such that a temperature of the liquid as uniform as possible over the whole length of the cavity 128 is obtained.

A second section 140 of the tube 127 defining the cavity 128 is surrounded by cooling means in the form of a liquid cooler 142. The liquid is cooled down to a temperature below the atmospheric boiling point by the liquid cooler 142. In the case that the tube is a quartz tube (6 or 8 mm outer diameter, 0.5 or 1 mm inner diameter, 1 m total length), the first section 130 is heated indirectly. High pressure resistant plastics adaptors for connection to conventional HPLC standard connectors are attached to the cold ends of the quartz tube, for example by cementing. Then vapor-free liquid emerges from the restrictor 130. The outlet side of the cavity 128 is connected to the restrictor 130 through an adapter 144 and an inert hose 146. A protective filter 148 similar to the filter 26 of FIG. 1 is provided on the inlet side of the restrictor 130. A cap recombining means 150 is placed on the housing of the restrictor 130, the cap serving to recombine the aerosol and the liquid digestant jet emerging from the restrictor and to form a uniform liquid stream issuing from the throughbore 151. From here, the liquid flow can be directed to individual collecting vessels or a fraction collector. Since a low-pressure liquid stream issues from the restrictor 130, automatic on-line determination methods like photometric determinations or atomic absorption determinations in accordance with the hydride or cold vapor method, can be employed with the use of known low pressure flow systems following downstream.

The restrictor 130 may also be a capillary. The capillary may have an inner diameter of 50 $\mu$m and a length between 50 mm and 500 mm, depending on the flow rate and the desired back pressure.

Without the cap 150, the restrictor 130 may be used for high pressure nebulization and for the introduction of aerosol into an analytical atomic spectrometer as described hereinbefore with reference to FIGS. 1 to 4 in connection with the restrictor 30. In this way, the assembly of FIG. 6 can be used twofold, namely for sample digestion by passing sample liquid together with the liquid digestant through the heated cavity under high pressure preventing vaporization of the liquids and, at the same time, for nebulizing the digested sample liquid by means of a restrictor following the cavity. The restrictor, on the one hand, ensures the pressure in the cavity to be maintained and, on the other hand, causes nebulization of the liquid. In the illustrated arrangement, the sample liquid is cooled between the digestion and the nebulization. Of course, the nebulization can take place also in the absence of the second section on cooling means.

Figure 8:
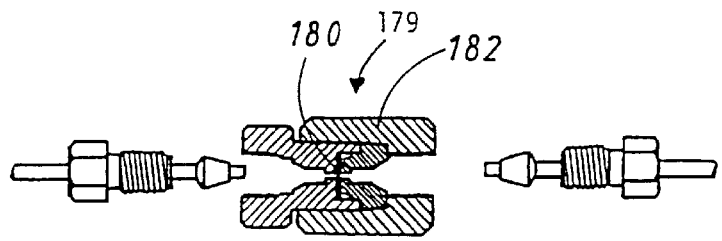
FIG. 8 shows a simple throughflow restrictor.

The restrictor may also be of the type illustrated in FIG. 8, the liquid being guided, on the low-pressure side, by an inert HPLC-hose connection (for example 1/16" PTFE-hose), as has been described hereinbefore.

A coarse physico-chemical rule says that chemical reactions double in their reaction rate for each 10K temperature increase. Therefore, the use of temperatures as high as possible reduces very much the required digestion time. The use of capillaries as digestion vessels, made possible here, permits operating at high pressures and, thereby, using also high temperatures without vapor development.

Figure 7:
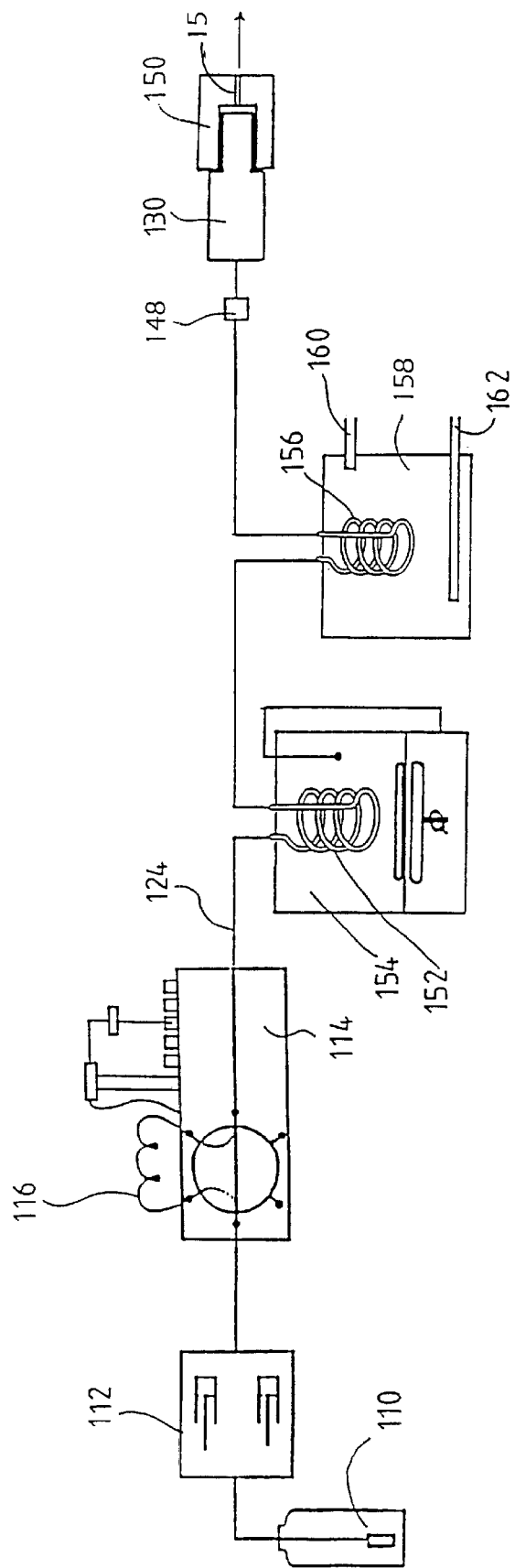
FIG. 7 shows a sample digesting system similar to FIG. 6.

The sample digesting system of FIG. 7 is of similar construction as the sample digesting system of FIG. 6. Corresponding elements are designated by the same reference numerals in both Figures and are no longer described in detail.

In the sample digesting system of FIG. 7, a first section of the cavity is formed by a coiled tube 152. This coiled tube 152 is placed in a thermostatted liquid heater bath 154. A similar second section forming a coiled tube 156 is connected to the first coiled tube 152 downstream thereof. The second coiled tube 156 is placed in a cooling bath 158. A continuous stream of coolant liquid is passed through the cooling bath through ports 160 and 162.

The liquid bath can be replaced by a heater oven, as, for example, commercially available for heating separating columns in high pressure liquid chromatography.

The restrictor 130 may be heatable. The connecting conduit 146 and the restrictor 30 or restrictor 130 may be thermally insulated.

In a device of FIG. 6 or 7, the restrictor 130 can also be arranged between the first or heated and the second or cooled section formed by the tube. In this case, the restrictor is designed as shown in FIG. 8.

In the arrangement shown in FIG. 8, the restrictor 179 comprises a restrictor body 180, which, for example, may be a lamina inserted in the conduit and provided with a narrow restrictor opening. The lamina is of substantially the same design as the lamina in the restrictor 30, which was described hereinbefore with reference to FIG. 2. The restrictor body 180 is held in a housing 182 adapted to be screwed together. The two ends of the housing 182 are provided with conventional connectors as used in high pressure liquid chromatography.

Figure 9:
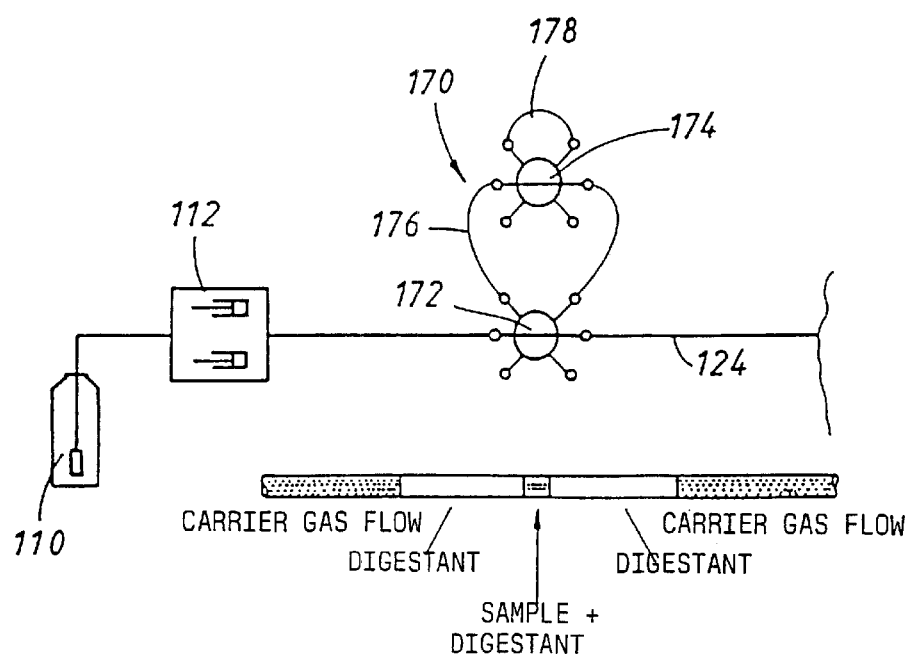
FIG. 9 shows a sampling device which permits embedding a sample liquid containing added digestant in a plug of pure digestant.

If a "plug" of a sample with added digestant were transported through the system by a pure carrier liquid such as water, there would be dilution of the digestant in the sample at the ends of the sample plug. If digestant is used as carrier liquid, in order to avoid this, as this is the case in the embodiment of FIG. 6, then the liquid digestant has to be fed by the high pressure pump 112, which would require a chemically inert high pressure pump. These problems can be avoided by the arrangement illustrated in FIG. 9. The arrangement of FIG. 9 is, to a large extent, identical with the corresponding arrangement of FIG. 6. Corresponding elements are designated by the same reference numerals as there.

In the arrangement of FIG. 9, an introduction device or infeed means 170 including a first valve 172 and a second valve 174 is provided between the high pressure pump 112 and the cavity 128. The first valve 172 is arranged to optionally insert a first loop 176 into the flow of liquid from the high pressure pump 112 to the cavity. The first loop contains the second valve 174. The second valve 174 is arranged to optionally insert a second loop 178 into the first loop 176. The sample liquid with added digestant is filled into the second loop 178. The first loop contains digestant. After the two loops 176, 178 have been filled, the second loop can, at first, be connected into the first loop 176 by means of the second valve 174. Thereafter, the first loop 176 is connected by means of the first valve 172 into a carrier liquid flow from the high pressure pump 112 to the cavity. In this manner, there are sequentially introduced into the flow of carrier liquid, (i) liquid digestant, (ii) the sample, and (iii) liquid digestant so that the sample with added digestant is surrounded, at the ends of the sample plug, by digestant. There is no dilution of the digestant in the sample. On the other hand, a non-aggressive liquid, for example water, can be selected as carrier liquid.

What is claimed is:

1. An apparatus for handling flowing liquids, comprising:
a high pressure pump having an input side and an output side;
a source of liquid connected to said input side of said high pressure pump;
a tubular body defining a cavity having an inlet side connecting to a first section of the cavity, an outlet side connecting to a second section of the cavity, and a substantially uniform cross-sectional area;
said output side of said high pressure pump being connected to said body at said inlet side of said cavity;
a capillary flow restrictor connected to said body at said outlet side of said cavity, said flow restrictor having an opening through which the liquid is expelled having a cross-sectional area;
heating means associated with the first section of the cavity for heating said first section of the cavity to a predetermined temperature sufficient to cause vaporization of liquid flowing in said first section of the cavity at atmospheric pressure;

cooling means associated with the second section of the cavity for cooling said second section of the cavity to a predetermined temperature sufficient to cool the liquid flowing in said second section of the cavity below the boiling point of said liquid at atmospheric pressure;

said liquid pumped through said cavity and said flow restrictor under the action of said high pressure pump; and said cross-sectional areas of said cavity and said opening of said flow restrictor being of such a ratio relative to a predetermined flow rate of the liquid through said cavity that said flow restrictor has a flow resistance sufficient to build up the pressure prevailing in said cavity to a level in excess of the saturated vapor pressure of said liquid at said predetermined temperature, such that no vapor and crystallized depositions occur in said cavity at said predetermined temperature, and such that at least a portion of liquid which exits from said cavity through said flow restrictor is nebulized to an aerosol by means of the reduction in pressure from that prevailing in said cavity to atmospheric pressure causing expansion and vaporization thereof.

2. The apparatus as defined in claim 1, wherein:

said flow restrictor comprises a restrictor body defining a restrictor opening which has a diameter and a length; and said diameter and said length defining a diameter-to-length ratio selected to cause turbulent flow through said restrictor opening.

3. The apparatus as defined in claim 2, wherein;

said flow restrictor includes a narrowest throughflow section defining a length and a diameter; and said length of said narrowest throughflow section being selected to be either (i) equal to or (ii) smaller than said diameter of said narrowest throughflow section.

4. The apparatus as defined in claim 3, wherein:

said narrowest throughflow section of said restrictor body defines a cross-sectional area;

said cross-sectional area having a value lower than 1.3 $10^{-9}$ m$^2$; and said pressure, which prevails in said cavity, has a value in excess of 3 MPa.

5. The apparatus as defined in claim 2, wherein:

said restrictor body constitutes a lamina having a predetermined thickness and a stepped throughbore;

said stepped throughbore defining said restrictor opening which has a predetermined length, and a remaining portion of said throughbore;

said predetermined thickness of said lamina exceeding said predetermined length of said restrictor opening; and said remaining portion of said stepped throughbore tapering toward said restrictor opening.

6. The apparatus as defined in claim 1, wherein:

said body defining said cavity constitutes a hollow body having the shape of a tube;

said tube being made of a chemically highly resistant material which is electrically non-conductive; and said heating means comprising a heating coil surrounding said tube and connected to a source of electric energy.

7. The apparatus as defined in claim 1, wherein:

said tube is made of a chemically highly resistant material;

said tube having the shape of a capillary coil; and said heating means comprising a heat transfer medium into which said capillary coil is immersed.

8. The apparatus as defined in claim 1, wherein:

said tube is made of a chemically highly resistant material which is electrically conductive; and said heating means comprising a source of electrical energy connected to said tube.

9. The apparatus as defined in claim 8, wherein said tube is made of a platinum-iridium alloy.

10. The apparatus as defined in claim 1, further including:

infeed means interposed between said output side of said high pressure pump and said inlet side of said cavity;

said source of liquid connected to said input side of said high pressure pump constituting a carrier liquid reservoir; and said infeed means including a sample loop for infeeding a liquid sample into said carrier liquid which is pumped by said high pressure pump into said cavity.

11. The apparatus as defined in claim 10, wherein:

said flow restrictor comprises a restrictor opening; and said flow restrictor generating on the outlet side of said restrictor opening an aerosol of said liquid sample.

12. The apparatus as defined in claim 10, wherein said source of liquid connected to said input side of said high pressure pump constitutes a liquid digestant reservoir.

13. The apparatus as defined in claim 10, wherein:

said infeed means containing a first loop including first valve means and second valve means, and a second loop;

said first valve means selectively connecting said first loop to said inlet side of said cavity;

said second valve means selectively connecting said second loop and said first loop;

said first loop containing a liquid digestant; and said second loop containing said liquid sample and said liquid digestant.

14. The apparatus as defined in claim 11, further including:

drying means connected to said flow restrictor;

said liquid sample comprising a solid sample dissolved in a liquid solvent;

said aerosol substantially containing said solid sample;

said drying means comprising a heating chamber connected to said restrictor opening for vaporizing any solvent which is present in said aerosol issuing from said restrictor opening; and said drying means further comprising a cooling chamber following said heating chamber for removing by condensation said solvent vaporized in said heating chamber.

15. The apparatus as defined in claim 11, further including:

an atomic spectrometer comprising an atomizer for receiving and atomizing a sample; and said atomizer receiving said aerosol issuing from said restrictor opening.

16. The apparatus as defined in claim 15, wherein:

said atomizer comprises a burner and a mixing chamber connected to a source of combustible gas; and said restrictor opening extending into said mixing chamber for mixing said aerosol and said combustible gas.

17. The apparatus as defined in claim 14, further including:

an atomic spectrometer comprising a plasma burner for atomizing a sample; and said drying means being connected to said plasma burner for feeding dried aerosol to said plasma burner.

18. The apparatus as defined in claim 10, further including:

a high pressure separating column interposed between said infeed means and said cavity; and a high pressure valve assembly interconnecting said high pressure separating column and said cavity.

19. The apparatus as defined in claim 12, additionally including recombining means connected to said restrictor opening for recombining aerosol and liquid issuing from said restrictor opening and forming therefrom a uniform liquid flow.

20. The apparatus as defined in claim 19, wherein:

said first section of said body is in the form of a first coiled tube;

said heating means comprising a heating bath in which said first coiled tube is immersed;

said second section of said body being in the form of a second coiled tube; and said cooling means comprising a cooling bath in which said second coiled tube is immersed.

21. A method of handling a flowing liquid, comprising the steps of:

pumping a flow of liquid under pressure through a hollow body defining a cavity having an inlet side, an outlet side, and a substantially uniform cross-sectional area;

providing a flow resistance on the outlet side of said cavity by providing a flow restrictor having an opening through which the liquid is expelled having a cross-sectional area through which the liquid must flow, said cross-sectional areas of said cavity and said opening of said flow restrictor being of such a ratio relative to a predetermined flow rate of the liquid through said cavity thereby building up high pressure in said cavity with respect to atmospheric pressure;

during said step of pumping said flow of liquid through said cavity, heating said liquid in said cavity to a predetermined temperature sufficient to cause vaporization of said liquid at atmospheric pressure by means of heating said hollow body;

wherein said step of building up said high pressure in said cavity entails generating a pressure in excess of the saturated vapor pressure of said liquid at said predetermined temperature such that no vapor and crystallized depositions occur in said cavity at said predetermined temperature; and generating an aerosol of liquid by nebulizing at least a portion of liquid exiting from said flow resistance by means of the reduction in pressure from that prevailing in said cavity to atmospheric pressure causing expansion and vaporization thereof.

22. The method as defined in claim 21, wherein:

said step of heating said liquid in said cavity entails electrically heating said hollow body; and automatically controlling said predetermined temperature by regulating the electric heating power supplied for electrically heating said hollow body.

23. The method as defined in claim 21, wherein:

said step of heating said liquid in said cavity includes immersing said hollow body in a heating bath; and automatically controlling said predetermined temperature by thermostatting said heating bath.

24. The method as defined in claim 21, further including the steps of:

selecting as said liquid, a carrier liquid;

during said step of pumping said flow of liquid through said cavity, pumping a flow of said carrier liquid through said cavity; and prior to said step of pumping said flow of carrier liquid through said cavity, infeeding a liquid sample into said flow of carrier liquid.

25. The method as defined in claim 24, wherein said step of selecting said carrier liquid entails selecting a liquid digestant as said carrier liquid.

26. The method as defined in claim 24, wherein said step of infeeding said liquid sample into said flow of carrier liquid entails sequentially infeeding a liquid digestant, a mixture of said liquid digestant and said liquid sample, and said liquid digestant into said flow of carrier liquid.

27. The method as defined in claim 24, further including the step of generating an aerosol of said liquid sample on the outlet side of said flow resistance.

28. The method as defined in claim 27, further including the step of feeding the aerosol to an atomizer of an atomic spectrometer.

29. The method as defined in claim 28, further including the steps of:

selecting as said atomizer of said atomic spectrometer a burner including a mixing chamber;

feeding a combustible gas to said mixing chamber of said burner; and said step of feeding said aerosol to said atomizer of said atomic spectrometer entails infeeding said aerosol into said mixing chamber.

30. The method as defined in claim 28, further including the steps of:

dissolving a solid sample in a solvent and thereby forming a liquid solution;

said step of infeeding said liquid sample into said flow of carrier liquid encompasses infeeding said liquid solution into said flow of carrier liquid;

drying said aerosol prior to the step of feeding the same to said atomizer of said atomic spectrometer; and during said step of drying said aerosol, heating said aerosol for vaporizing said solvent in which said solid sample is dissolved, and cooling the heated aerosol and thereby condensing said solvent.

31. The method as defined in claim 30, further including the steps of:

selecting a plasma burner as said atomizer of said atomic spectrometer; and feeding said dried aerosol to said plasma burner.

32. The method as defined in claim 24, further including the step of passing the flow of liquid containing said liquid sample through a high pressure separating column prior to pumping said flow of liquid containing said liquid sample through said cavity.

33. The method as defined in claim 25, further including the steps of:

subdividing said hollow body defining said cavity into a heating section and a cooling section following said heating section in the direction of flow of said liquid digestant;

selecting as said predetermined temperature in said heating section, a temperature sufficient for digesting said liquid sample;

cooling said heated flow of liquid digestant in said cooling section to a temperature below the boiling point of said liquid digestant under atmospheric pressure; and producing a substantially uniform liquid flow issuing on the outlet side of said flow resistance by recombining said aerosol and said liquid digestant on the outlet side of said flow resistance.

34. The method as defined in claim 26, further including the steps of:
   subdividing said hollow body defining said cavity into a heating section and a cooling section following said heating section in the direction of flow of said carrier liquid;
   selecting as said predetermined temperature in said heating section, a temperature sufficient for digesting said liquid sample;
   cooling said heated flow of carrier liquid in said cooling section to a temperature below the boiling point of said carrier liquid under atmospheric pressure; and
   producing a substantially uniform liquid flow issuing on the outlet side of said flow resistance by recombining said aerosol and said carrier liquid on the outlet side of said flow resistance.

35. An apparatus for handling liquids, comprising:
   a high pressure pump having an input side and an output side;
   a carrier liquid reservoir connected to said input side of said high pressure pump;
   a tubular body defining a cavity having an inlet side connecting to a first section of the cavity, an outlet side connecting to a second section of the cavity, and a substantially uniform cross-sectional area;
   said output side of said high pressure pump being connected to said body at said inlet side of said cavity with infeed means interposed therebetween;
   said infeed means including a sample loop for infeeding a liquid sample into said carrier liquid which is pumped by said high pressure pump into said cavity, said infeed means comprising;
      a first loop including first valve means and second valve means, and a second loop;
      said first valve means selectively connecting said first loop to said inlet side of said cavity;
      said second valve means selectively connecting said second loop and said first loop;
      said first loop containing a liquid digestant; and
      said second loop containing said liquid sample and said liquid digestant;
   a capillary flow restrictor connected to said outlet side of said cavity, said flow restrictor having an opening through which the liquid is expelled having a cross-sectional area;
   heating means associated with the first section of the cavity for heating said said first section of the cavity to a predetermined temperature sufficient for digestion of said liquid sample and to cause vaporization of liquid in said first section of the cavity at atmospheric pressure;
   cooling means associated with the second section of the cavity for cooling said second section of the cavity to a predetermined temperature sufficient to cool the liquid flowing in said second section of the cavity below the boiling point of said liquid at atmospheric pressure;
   said liquid pumped through said cavity and said flow restrictor under the action of said high pressure pump; and
   said cross-sectional areas of said cavity and said opening of said flow restrictor being of such a ratio relative to a predetermined flow rate of the liquid through said cavity that said flow restrictor has a flow resistance sufficient to build up the pressure prevailing in said cavity to a level in excess of the saturated vapor pressure of said liquid at said predetermined temperature such that no vapor and crystallized depositions occur in said cavity at said predetermined temperature, such that said liquid sample is digested within said cavity by said liquid digestant, and such that at least a portion of liquid including said liquid sample which exits from said cavity through said flow restrictor is nebulized to an aerosol by means of the reduction in pressure from that prevailing in said cavity to atmospheric pressure causing expansion and vaporization thereof.

36. An apparatus for handling liquids, comprising:
   a high pressure pump having an input side and an output side;
   a liquid digestant reservoir connected to said input side of said high pressure pump;
   a tubular body comprising a first section and a second section defining a cavity having an inlet side, an outlet side, and a substantially uniform cross-sectional area;
   said output side of said high pressure pump being connected to said body at said inlet side of said cavity with infeed means interposed therebetween;
   said infeed means including a sample loop for infeeding a liquid sample into said liquid digestant which is pumped by said high pressure pump into said cavity;
   a flow restrictor connected to said body at said outlet side of said cavity, said flow restrictor having a restrictor opening through which the liquid is expelled having a cross-sectional area;
   heating means disposed adjacent said first section of said body for heating said first section of said body to a predetermined temperature sufficient for digestion of said liquid sample in said cavity and to cause vaporization of liquid at atmospheric pressure pumped through said cavity and said flow restrictor under the action of said high pressure pump;
   cooling means for cooling said second section of said body to a temperature below the boiling point of said liquid digestant in said cavity under atmospheric pressure;
   said cross-sectional areas of said cavity and said opening of said flow restrictor being of such a ratio relative to a predetermined flow rate of the liquid through said cavity that said flow restrictor has a flow resistance sufficient to build up the pressure prevailing in said cavity to a level in excess of the saturated vapor pressure of said liquid at said predetermined temperature such that no vapor and crystallized deposition occur in said cavity at said predetermined temperature, such that said liquid sample is digested within said cavity by said liquid digestant, and such that at least a portion of liquid including said liquid sample which exits from said cavity through said flow restrictor is nebulized to an aerosol by means of reduction in pressure from that prevailing in said cavity to atmospheric pressure causing expansion and vaporization thereof; and
   recombining means connected to said restrictor opening for recombining aerosol and liquid issuing from said restrictor opening and forming therefrom a uniform liquid flow.

37. The apparatus as defined in claim 36, wherein:
said first section of said body is in the form of a first coiled tube;
said heating means comprises a heating bath in which said first coiled tube is immersed;
said second section of said body being in the form of a second coiled tube; and
said cooling means comprises a cooling bath in which said second coiled tube is immersed.

38. A method of handling a liquid, comprising the steps of:
selecting as the liquid, a carrier liquid;
infeeding a liquid sample into a flow of said carrier liquid;
pumping a flow of said carrier liquid under high pressure through a hollow body defining a cavity having an inlet side, an outlet side, and a substantially uniform cross-sectional area;
providing a flow resistance on the outlet side of said cavity by providing a flow restrictor having an opening through which the liquid is expelled having a cross-sectional area through which the liquid must flow, said cross-sectional areas of said cavity and said opening of said flow restrictor being of such a ratio relative to a predetermined flow rate of the liquid through said cavity thereby building up high pressure in said cavity with respect to atmospheric pressure;
during said step of pumping said flow of carrier liquid through said cavity, heating said liquid in said cavity to a predetermined temperature sufficient to cause vaporization of said liquid in said cavity at atmospheric pressure by means of heating said hollow body;
wherein said step of building up said high pressure in said cavity entails generating a pressure in excess of the saturated vapor pressure of said carrier liquid at said predetermined temperature such that no vapor and crystallized depositions occur in said cavity at said predetermined temperature;
generating an aerosol of said liquid sample by nebulizing at least a portion of liquid including said liquid sample exiting from said flow resistance by means of the reduction in pressure from that prevailing in said cavity to atmospheric pressure causing expansion and vaporization thereof;
selecting an atomizer for an atomic spectrometer of the type having a burner including a mixing chamber;
feeding a combustible gas to said mixing chamber of said burner; and
infeeding said aerosol into said mixing chamber.

39. A method of handling a liquid, comprising the steps of:
selecting as the liquid, a carrier liquid;
dissolving a solid sample in a solvent and thereby forming a liquid solution;
infeeding said liquid solution into a flow of said carrier liquid;
pumping a flow of said carrier liquid under high pressure through a hollow body defining a cavity having an inlet side, an outlet side, and a substantially uniform cross-sectional area;
providing a flow resistance on the outlet side of said cavity by providing a flow restrictor having an opening through which the liquid is expelled having a cross-sectional area through which the liquid must flow, said cross-sectional areas of said cavity and said opening of said flow restrictor being of such a ratio relative to a predetermined flow rate of the liquid through said cavity thereby building up high pressure in said cavity with respect to atmospheric pressure;
during said step of pumping said flow of carrier liquid through said cavity, heating said liquid in said cavity to a predetermined temperature sufficient to cause vaporization of said liquid in said cavity at atmospheric pressure by means of heating said hollow body;
wherein said step of building up said high pressure in said cavity entails generating a pressure in excess of the saturated vapor pressure of said carrier liquid at said predetermined temperature such that no vapor and crystallized depositions occur in said cavity at said predetermined temperature;
generating an aerosol of said liquid sample by nebulizing at least a portion of liquid including said liquid solution exiting from said flow resistance by means of the reduction in pressure from that prevailing in said cavity to atmospheric pressure causing expansion and vaporization thereof;
drying said aerosol by heating said aerosol for vaporizing said solvent in which said solid sample is dissolved, and cooling the heated aerosol and thereby condensing said solvent; and
feeding said aerosol to an atomizer of an atomic spectrometer.

40. A method of handling a liquid, comprising the steps of:
selecting as the liquid, a carrier liquid comprising a liquid digestant;
infeeding a liquid sample into a flow of said liquid digestant;
subdividing a hollow body defining a cavity having an inlet side, an outlet side, and a substantially uniform cross-sectional area into a heating section and a cooling section following said heating section in the direction of flow of said liquid digestant;
pumping a flow of said liquid digestant under high pressure through said cavity;
providing a flow resistance on the outlet side of said cavity by providing a flow restrictor having an opening through which the liquid is expelled having a cross-sectional area through which the liquid must flow, said cross-sectional areas of said cavity and said opening of said flow restrictor being of such a ratio relative to a predetermined flow rate of the liquid through said cavity thereby building up high pressure in said cavity with respect to atmospheric pressure;
selecting as a predetermined temperature in said heating section, a temperature sufficient for causing vaporization of said liquid pumped through said cavity at atmospheric pressure and for digesting said liquid sample;
during said step of pumping said flow of liquid digestant through said cavity, heating said liquid in said cavity to said predetermined temperature by means of heating said heating section of said hollow body;
cooling said heated flow of liquid digestant in said cooling section to a temperature below the boiling point of said liquid digestant under atmospheric pressure by means of cooling said cooling section of said hollow body;
said step of building up said high pressure in said cavity entails generating a pressure in excess of the saturated vapor pressure of said liquid digestant at said predetermined temperature such that no vapor and crystallized depositions occur in said cavity at said predetermined temperature, such that said liquid sample is digested within said cavity by said liquid digestant;

generating an aerosol of said liquid sample by nebulizing at least a portion of liquid including said liquid sample exiting from said flow resistance by means of the reduction in pressure from that prevailing in said cavity to atmospheric pressure causing expansion and vaporization thereof; and producing a substantially uniform liquid flow issuing on the outlet side of said flow resistance by recombining said aerosol and liquid on the outlet side of said flow resistance.

41. A method of handling a liquid, comprising the steps of:

selecting as the liquid, a carrier liquid;

infeeding a liquid sample into a flow of said carrier liquid by sequentially infeeding a liquid digestant, a mixture of said liquid digestant and said liquid sample, and said liquid digestant into said flow of carrier liquid;

subdividing a hollow body defining a cavity having an inlet side, an outlet side, and a substantially uniform cross-sectional area into a heating section and a cooling section following said heating section in the direction of flow of said carrier liquid;

pumping said flow of said carrier liquid under high pressure through said cavity;

providing a flow resistance on the outlet side of said cavity by providing a flow restrictor having an opening through which the liquid is expelled having a cross-sectional area through which the liquid must flow, said cross-sectional areas of said cavity and said opening of said flow restrictor being of such a ratio relative to a predetermined flow rate of the liquid through said cavity thereby building up high pressure in said cavity with respect to atmospheric pressure;

selecting as a predetermined temperature in said heating section, a temperature sufficient for vaporizing said liquid in said cavity at atmospheric pressure and for digesting said liquid sample;

during said step of pumping said flow of carrier liquid through said cavity, heating said liquid in said cavity to a predetermined temperature by means of heating said heating section of said hollow body;

cooling said heated flow of carrier liquid in said cooling section to a temperature below the boiling point of said carrier liquid under atmospheric pressure by means of cooling said cooling section of said hollow body;

said step of building up said high pressure in said cavity entails generating a pressure in excess of the saturated vapor pressure of said carrier liquid at said predetermined temperature such that no vapor and crystallized depositions occur in said cavity at said predetermined temperature, such that said liquid sample is digested within said cavity by said liquid digestant;

generating an aerosol of said liquid sample by nebulizing at least a portion of liquid including said liquid sample exiting from said flow resistance by means of the reduction in pressure from that prevailing in said cavity to atmospheric pressure causing expansion and vaporization thereof; and producing a substantially uniform liquid flow issuing on the outlet side of said flow resistance by recombining said aerosol and liquid on the outlet side of said flow resistance.

* * * * *

Disclaimer

6,528,018 B1 — Harold Berndt, Dortmund (DE). DEVICE FOR HANDLING LIQUIDS FOR ANALYTICAL PURPOSES. Patent dated Mar. 4, 2003, Disclaimer filed Aug. 27, 2004, by the Assignee, Roche Diagnostic, Inc.

This patent is subject to a terminal disclaimer.

*(Official Gazette June 14, 2005)*